(12) United States Patent
Merrick et al.

(10) Patent No.: US 12,716,186 B2
(45) Date of Patent: Aug. 25, 2026

(54) COMPLEX SOIL ROTATIONAL PENETROMETER DEVICE

(71) Applicant: The Government of the United States of America, as represented by the Secretary of the Navy, Arlington, VA (US)

(72) Inventors: Trina L. Merrick, Stevensville, MD (US); Andrei Abelev, McLean, VA (US); Michael S. Vermillion, Crofton, MD (US)

(73) Assignee: The Government of the United States of America, as represented by the Secretary of the Navy, Arlington, VA (US)

( * ) Notice: Subject to any disclaimer, the term of this patent is extended or adjusted under 35 U.S.C. 154(b) by 273 days.

(21) Appl. No.: 18/630,180

(22) Filed: Apr. 9, 2024

(65) Prior Publication Data

US 2024/0344288 A1 Oct. 17, 2024

Related U.S. Application Data

(60) Provisional application No. 63/458,672, filed on Apr. 12, 2023.

(51) Int. Cl.
*E02D 1/00* (2006.01)
*E02D 1/02* (2006.01)
(Continued)

(52) U.S. Cl.
CPC .............. *E02D 1/00* (2013.01); *E02D 1/022* (2013.01); *G01L 5/0038* (2013.01);
(Continued)

(58) Field of Classification Search
CPC ....... E02D 1/00; E02D 1/022; E02D 2600/10; E02D 2600/30; G01L 5/0038; G01L 5/0042; G01N 3/42; G01N 33/24
See application file for complete search history.

(56) References Cited

U.S. PATENT DOCUMENTS 3,797,301 A * 3/1974 Hawes .................... E02D 1/022 73/843
4,685,339 A * 8/1987 Philipenko ............. E21B 10/04 175/203

(Continued)

FOREIGN PATENT DOCUMENTS

CN 103115832 A * 5/2013
CN 104535488 A * 4/2015

(Continued)

OTHER PUBLICATIONS

CN-103115832-A, English Translation (Year: 2013).*

(Continued)

*Primary Examiner* — Ryan D Walsh
(74) *Attorney, Agent, or Firm* — US Naval Research Laboratory; Suresh Koshy

(57) ABSTRACT

An apparatus includes a head having an obverse side and a reverse side. The apparatus includes a vertical load cell detachably connected to the obverse side. The vertical load cell in operation measures a plurality of vertical loads at a respective plurality of ground depths. The apparatus includes a plurality of pins connected to the reverse side. Each pin of the plurality of pins includes a rod and a cone connected to the rod. The apparatus includes a torsional load cell detachably connected to the obverse side. The torsional load cell in operation measures a plurality of torques at a respective plurality of rotational angles.

16 Claims, 19 Drawing Sheets

(51) Int. Cl.
*G01L 5/00* (2006.01)
*G01N 3/42* (2006.01)
*G01N 33/24* (2006.01)

(52) U.S. Cl.
CPC .............. *G01L 5/0042* (2013.01); *G01N 3/42* (2013.01); *G01N 33/24* (2013.01); *E02D 2600/10* (2013.01); *E02D 2600/30* (2013.01)

(56) References Cited

U.S. PATENT DOCUMENTS

| | | | | |
|---|---|---|---|---|
| 5,726,349 A * | 3/1998 | Palmertree | G01N 3/40 | 73/84 |
| 6,260,633 B1 * | 7/2001 | Machek | E21B 7/006 | 73/864.45 |
| 7,243,526 B2 * | 7/2007 | Pringle | G01N 3/48 | 73/12.09 |
| 2020/0109533 A1 * | 4/2020 | Mulla | G01N 3/34 | |

FOREIGN PATENT DOCUMENTS

| | | | | |
|---|---|---|---|---|
| CN | 106120693 A | * | 11/2016 | E02D 1/00 |
| JP | 2003227786 A | * | 8/2003 | |
| KR | 102080767 B1 | * | 5/2020 | G01L 5/0028 |
| MY | 175047 A | * | 6/2020 | |

OTHER PUBLICATIONS

CN-104535488-A, English Translation (Year: 2015).*
CN-106120693-A, English Translation (Year: 2016).*
JP-2003227786-A, English Translation (Year: 2003).*
KR-102080767-B1, English Translation (Year: 2020).*
MY-175047-A, English Translation (Year: 2020).*
Qiao, Huanhuan, The Practice and Development of T-Bar Penetrometer Tests in Offshore Engineering Investigation: A Comprehensive Review, Journal of Marine Science and Engineering, Jun. 1, 2023, pp. 1-31, vol. 11, No. 6, MDPI, Basel, Switzerland.
Kayabali, K., et al., Shear strength of remolded soils at consistency limits, Canadian Geotechnical Journal, 2010, pp. 259-266, vol. 47, No. 3, Canadian Publishing Science, Ottawa, Ontario, Canada.
O'Kelly, Brendan C., Atterberg limits and remolded shear strength—Water content relationships. Geotechnical Testing Journal, 2013, pp. 939-947, vol. 36, No. 6, ASTM, West Conshohocken, PA, USA.
Wu, Po-Kai, et al., Effects of specimen size and some other factors on the strength and deformation of granular soil in direct shear tests, Geotechnical Testing Journal, 2008, pp. 45-64, vol. 31, No. 1, Canadian Publishing Science, Ottawa, Ontario, Canada.
Randolph, M. F., "Characterization of soft sediments for offshore applications," Proceedings of the Second International Conference on Site Characterization, ISC-2, Sep. 19-22, 2004, pp. 209-231, International Society for Soil Mechanics and Geotechnical Engineering, Porto, Portugal.
Chaney, R. C. et al., "Measurement of residual/remolded vane shear strength of marine sediments," Vane Shear Strength Testing in Soils: Field and Laboratory Studies, 1988, pp. 166-181, American Society for Testing and Materials, West Conshohocken, PA, USA.
ASTM Standard D2573, "Standard Test Method for Field Vane Shear Test in Cohesive Soil," 2008, doi: DOI: 10.1520/C0033-03A, ASTM International, West Conshohocken, PA, USA.
Sasser, C.E. et al., Relationships of Marsh Soil Strength to Belowground Vegetation Biomass in Louisiana Coastal Marshes, Wetlands, Dec. 27, 2017, pp. 401-409, vol. 38, Springer Publishing, New York City, NY, USA.
Jafari, Navid H. et al., Wetland Shear Strength with Emphasis on the Impact of Nutrients, Sediments, and Sea Level Rise, Estuarine, Coastal and Shelf Science, Sep. 5, 2019, pp. 1-27, vol. 229, Elsevier, Amsterdam, Netherlands.
Berger, Perrine, et al., RF Spectrum Analyzer for Pulsed Signals: Ultra-Wide Instantaneous Bandwidth, High Sensitivity, and High Time-Resolution, Journal of Lightwave Technology, Oct. 15, 2016, pp. 4658-4663, vol. 34, No. 20, Optical Society and the IEEE Photonics Society, Washington, DC, USA.
Sefler, George A., et al., Demonstration of speckle-based compressive sensing system for recovering RF signals, Optics Express, Aug. 20, 2018, pp. 21390-21402, vol. 26, No. 17, Optica, Washington, DC, USA.
Wan, Yangyang, et al., Wavemeter Capable of Simultaneously Achieving Ultra-High Resolution and Broad Bandwidth by Using Rayleigh Speckle From Single Mode Fiber, Journal of Lightwave Technology, Apr. 1, 2021, pp. 2223-2229, vol. 39, No. 7, Optical Society and the IEEE Photonics Society, Washington, DC, USA.

* cited by examiner

VERTICAL DISPLACEMENT TRANSDUCER

LINEAR VARIABLE DIFFERENTIAL TRANDUCER

150

152

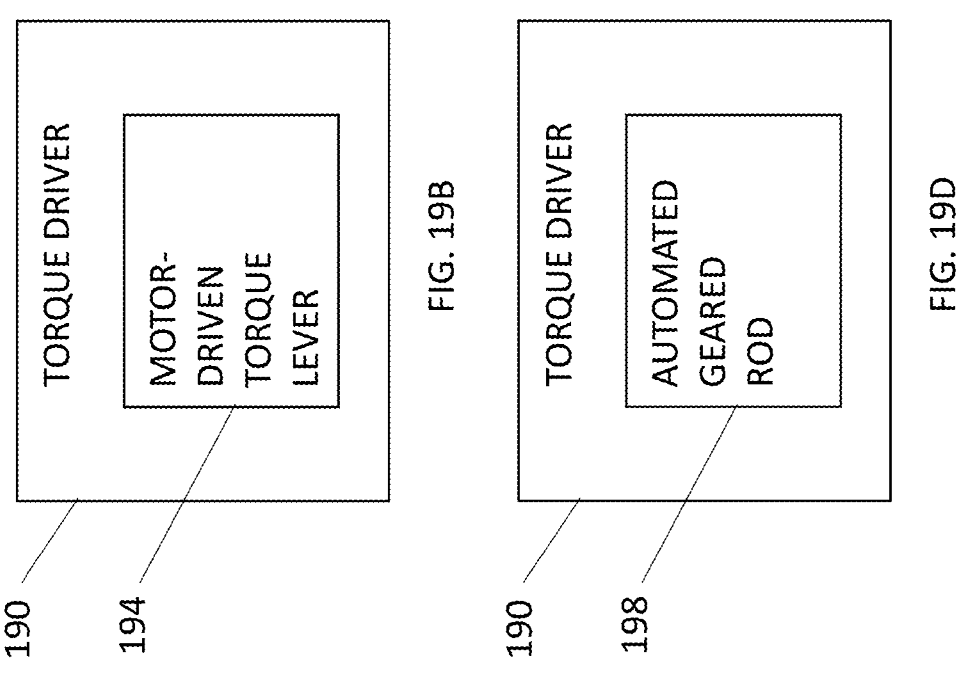
FIG. 19B
FIG. 19D
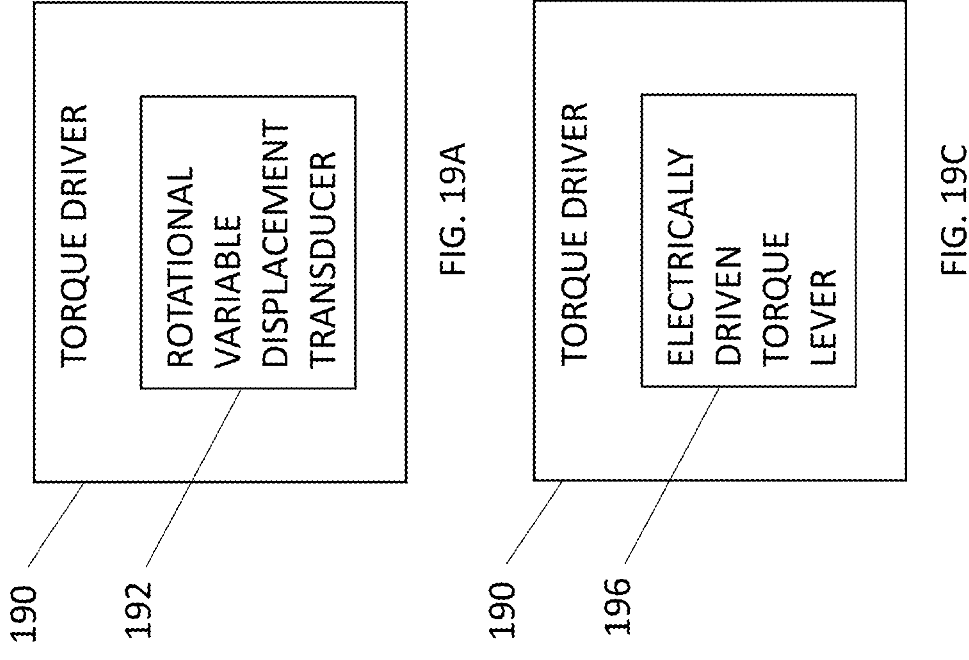
FIG. 19A
FIG. 19C

COMPLEX SOIL ROTATIONAL PENETROMETER DEVICE

CROSS-REFERENCE TO RELATED APPLICATIONS

This Application is a Non-provisional of, and claims the benefit of priority under 35 U.S.C. § 119 based on, U.S. Provisional Patent Application No. 63/458,672 to Merrick et al. The Provisional Patent Application and all references cited herein are hereby incorporated by reference into the present disclosure in their entirety.

FEDERALLY SPONSORED RESEARCH AND DEVELOPMENT

The United States Government has ownership rights in this invention. Licensing inquiries may be directed to Office of Technology Transfer, US Naval Research Laboratory, Code 1004, Washington, D.C. 20375, USA; +1.202.767.7230; techtran@nrl.navy.mil, referencing Navy Case No. 211,544-US2.

BACKGROUND OF THE INVENTION

Aspects of the instant invention relate generally to geotechnical instrumentation and, more particularly, to geotechnical instrumentation for analyzing soil characteristics.

Conventional geotechnical instruments are designed for particular soil types. Soil is homogenous, if it has properties uniformly distributed through one or more of its layers. Homogenous soil contrasts with complex soil matrices that have discontinuous inclusions, e.g., vegetation or geotextiles. As examples of conventional geotechnical instruments, standard vanes are designed for cohesive, fine-clay or high-clay-content, soils, and standard cone penetrometers are designed for sands, clays or other homogeneous soil mixtures. These two instruments and their associated methods are dissimilar. Conventional geotechnical measurements do not have the ability to engage with complex soils, or soils mixed with discontinuous matter, above-ground vegetation, below-ground vegetation, and/or man-made or incorporated materials, such as geotextiles. Furthermore, initial shear failure of soils and remolding tests are both desired to characterize soils and these measurements are desirable at different depths. However, conventional geotechnical instruments, such as cone penetrometers, cannot measure initial shear failure as well as remolding across a broad array of soil complexes. Other conventional geotechnical instruments, such as vane shear devices, are designed to do so, but are limited to cohesive materials only, inapplicable to sands and other granular-dominated materials, and are limited to soils without any discontinuous inclusions.

SUMMARY OF THE INVENTION

An embodiment of the invention includes an apparatus for use in cohesive soil, sand, and/or mixtures, whether free of discontinuous inclusions, or with these, representing complex soil matrices.

An embodiment of the invention includes an apparatus capable of engaging with complex soils, mixed soils, above-ground vegetation above, below-ground vegetation, and/or man-made or incorporated materials, such as geotextiles.

An embodiment of the invention includes an apparatus that can measure initial shear failure (or strength) and remolded (or residual) shear strength of complex soils, mixed soils, above-ground vegetation above, below-ground vegetation, and/or man-made or incorporated materials, such as geotextiles.

An embodiment of the invention includes an apparatus to measure the shear strength and remolded strengths of complex soil matrices across many conditions and many compositions at a minimum of two depths, e.g., 3" and 6".

An embodiment of the invention includes an apparatus. The apparatus includes a head comprising an obverse side and a reverse side. The apparatus includes a vertical load cell detachably connected to the obverse side. The vertical load cell in operation measures a plurality of vertical loads at a respective plurality of ground depths. The apparatus includes a plurality of pins connected to the reverse side. Each pin of the plurality of pins includes a rod and a cone connected to the rod. The apparatus includes a torsional load cell detachably connected to the obverse side. The torsional load cell in operation measures a plurality of torques at a respective plurality of rotational angles.

BRIEF DESCRIPTION OF THE DRAWINGS

Aspects of the instant invention are described in the detailed description which follows, in reference to the noted plurality of drawings by way of non-limiting examples of exemplary embodiments of the instant invention.

FIG. 19A is a block diagram of a torque driver including a rotational variable displacement transducer in an embodiment of the instant invention.

FIG. 19B is a block diagram of a torque driver including a motor-driven torque lever in an embodiment of the instant invention.

FIG. 19C is a block diagram of a torque driver including an electrically driven torque lever in an embodiment of the instant invention.

FIG. 19D is a block diagram of a torque driver including an automated geared rod in an embodiment of the instant invention.

DETAILED DESCRIPTION

An embodiment of the invention includes a geotechnical apparatus 10. The geotechnical apparatus 10 includes a head 20, as shown by way of illustration in FIGS. 1 and 2. The head 20 includes an obverse side and a reverse side. In an embodiment of the invention, the head 20 is made of a standard metal. For example, the head 20 is made of aluminum. As another example, the head 20 is made of stainless steel, depending on the stiffness and/or rigidity needed to compensate for moments imparted to the head 20 by the rods (discussed below) during rotational loading, without inducing plastic or permanent deformation in the head material due to such loading. In an embodiment of the invention, the thickness of the head 20 is selected to accommodate pins (discussed below) to be embedded therein at sufficient distance to ensure that the pins remain perpendicular to the head during operation. For example, the thickness of the head 20 and/or depth of pin embedding is adjusted or selected for different depth of penetrating rods.

Figure 1:
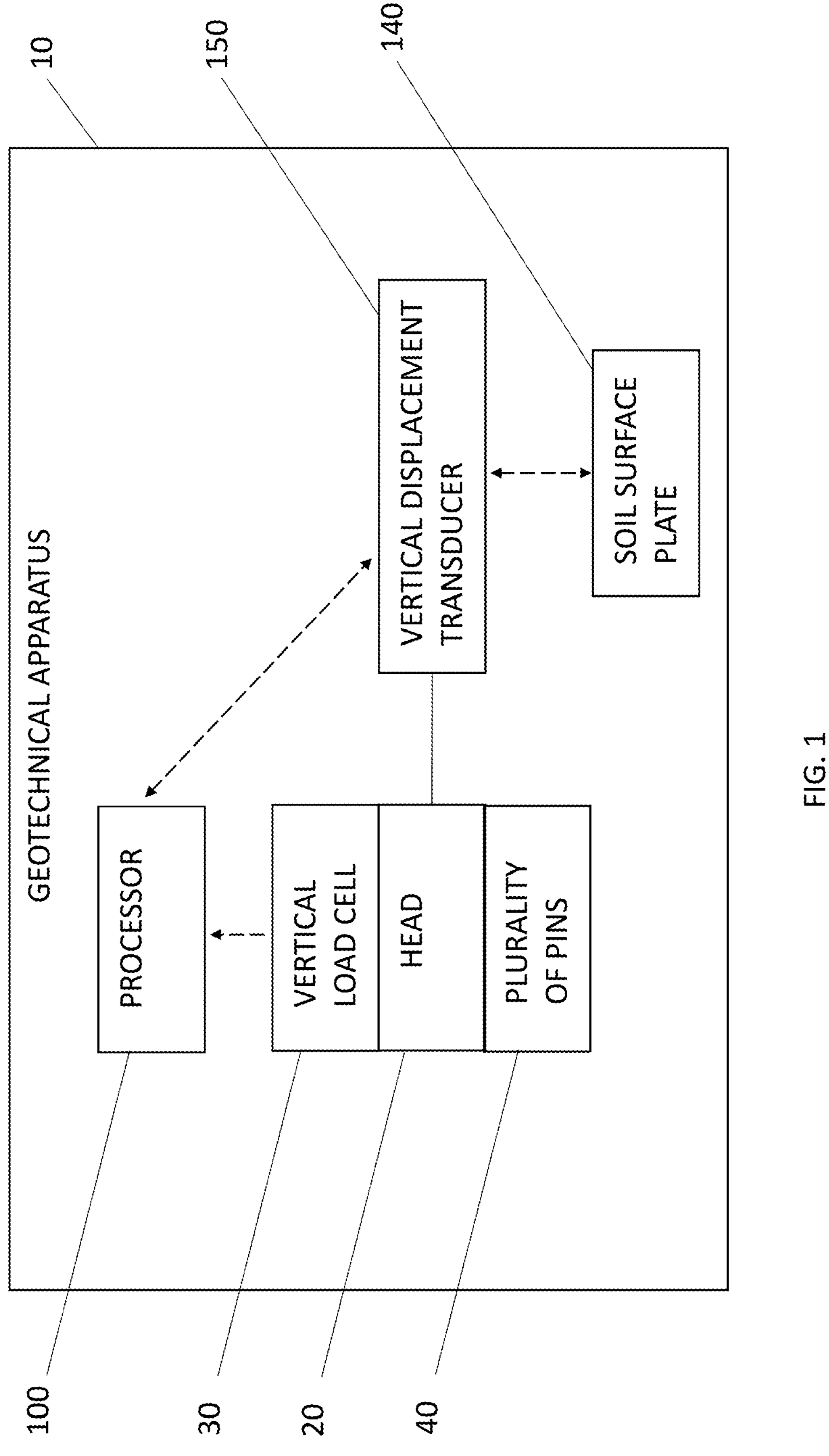
FIG. 1 is a block diagram of an embodiment of the instant invention, for example, for use in a vertical shear testing mode.

The geotechnical apparatus 10 includes a standard vertical load cell 30 detachably connected to the obverse side of the head 20, as shown by way of illustration in FIG. 1. The vertical load cell 30 in operation measures a plurality of vertical loads at a respective plurality of ground depths.

Figure 2:
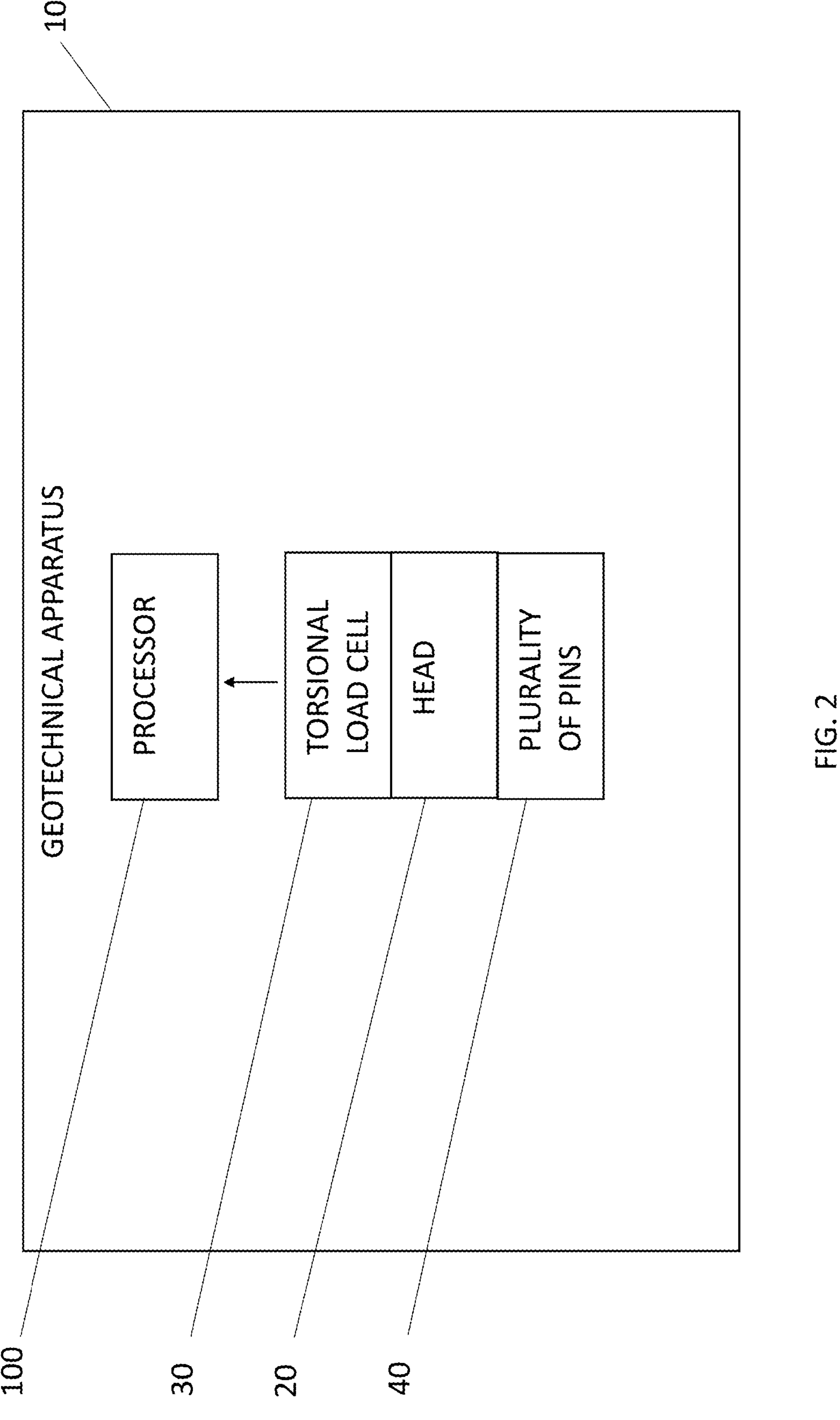
FIG. 2 is a block diagram of an embodiment of the instant invention, for example, for use in a rotational shear testing mode.
Figure 3:
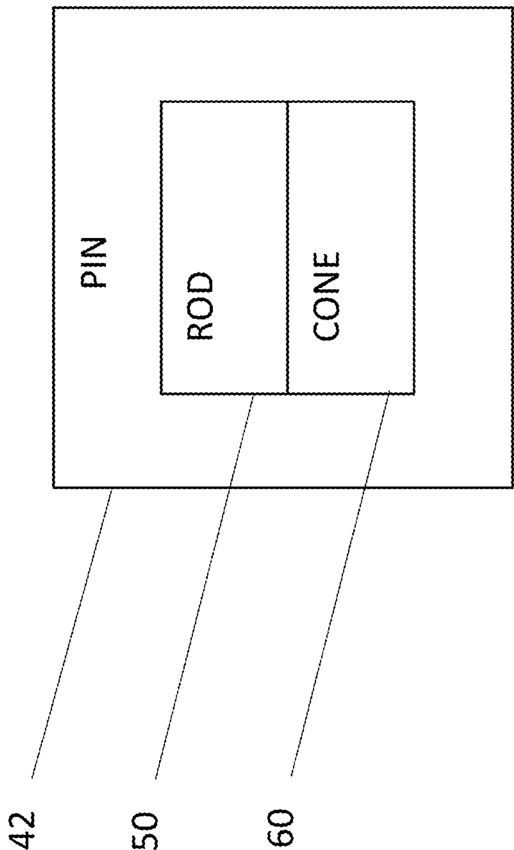
FIG. 3 is a block diagram of an illustrative pin in an embodiment of the instant invention.

The geotechnical apparatus 10 includes a plurality of pins 40 connected to the reverse side of the head 20, as shown by way of illustration in FIGS. 1 and 2. Each pin 42 of the plurality of pins 40 includes a rod 50 and a cone 60 connected to the rod, as shown by way of illustration in FIG. 3. In an embodiment of the invention, the pins 40 are made of a standard metal sufficient to resist abrasion from the soil complex to which the embodiment of the invention is applied. In an embodiment of the invention, the pins 40 are made of a standard metal sufficient to resist excessive deformations during the rotational stage of the loading, and to prevent from inducing any plastic (and possibly irreversible) deformations in the rods themselves, at maximum applied torque and maximum complex soil resistance scenarios. In an embodiment of the invention, the pins 40 are made of stainless steel. In an embodiment of the invention, the pins 40 are made of duplex stainless steel. Lengths of the rod 50 depend on the application. Rods in illustrative embodiments of the invention range from 6" to 18". For example, for assessing soil for off-road mobility of pedestrians or light vehicles (e.g., motorcycles, all-terrain vehicles, cars, and sport utility vehicles), an embodiment of the invention includes 6" rods. As another example, for assessing soil for heavy vehicles (e.g., agricultural vehicles, tanks, cargo trucks, helicopters, and/or aircraft), an embodiment of the invention includes rod with lengths ranging from 12" to 18". In an embodiment of the invention, cone diameters are dependent on the rod diameter, which is itself dependent on the maximum rod length selected; longer rod configurations, e.g. 18", correspond to larger rod diameters, e.g., 2", which then require cone base diameter to be, for example, 2.5" or 3", that is, larger than the diameter of the rods. In an embodiment of the invention, cone diameters depend on application. In illustrative embodiments of the invention, maximum cone diameters range from about 0.73" to about 2". Cone lengths in illustrative embodiments of the invention are dependent on the selected cone angle (e.g., a 30° apex angle or a 60° apex angle), and the cone base diameter is dictated by the rod diameter, as discussed above.

Figure 4:
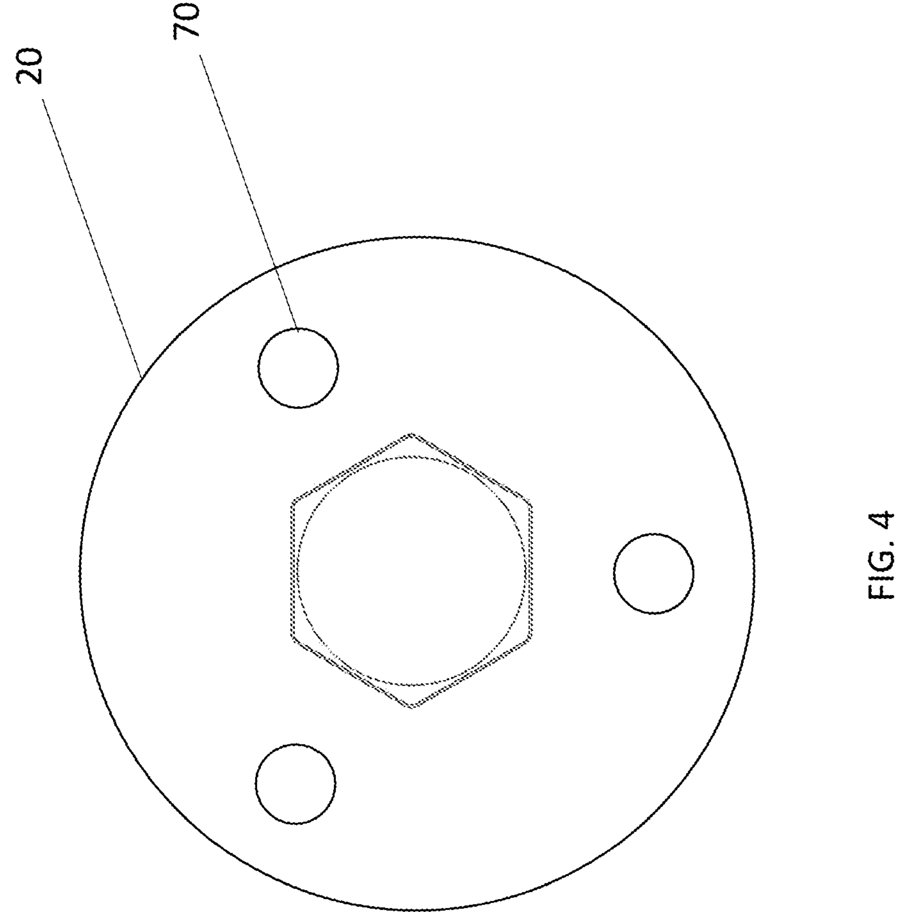
FIG. 4 is a top plan view of an embodiment of the instant invention.
Figure 5:
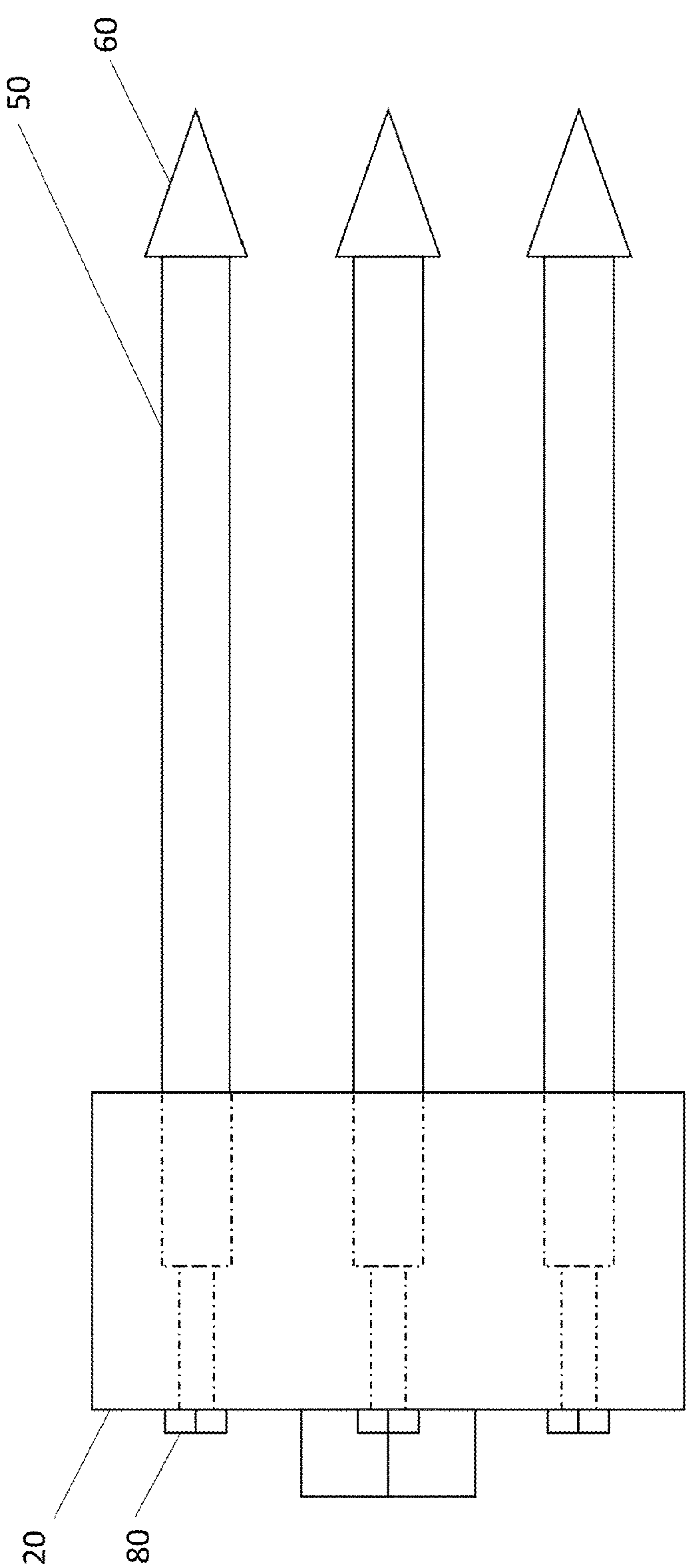
FIG. 5 is a side view of an embodiment of the instant invention, wherein rods extend into a head from a reverse side thereof and are affixed to the head, for example, by respective bolts.
Figure 6:
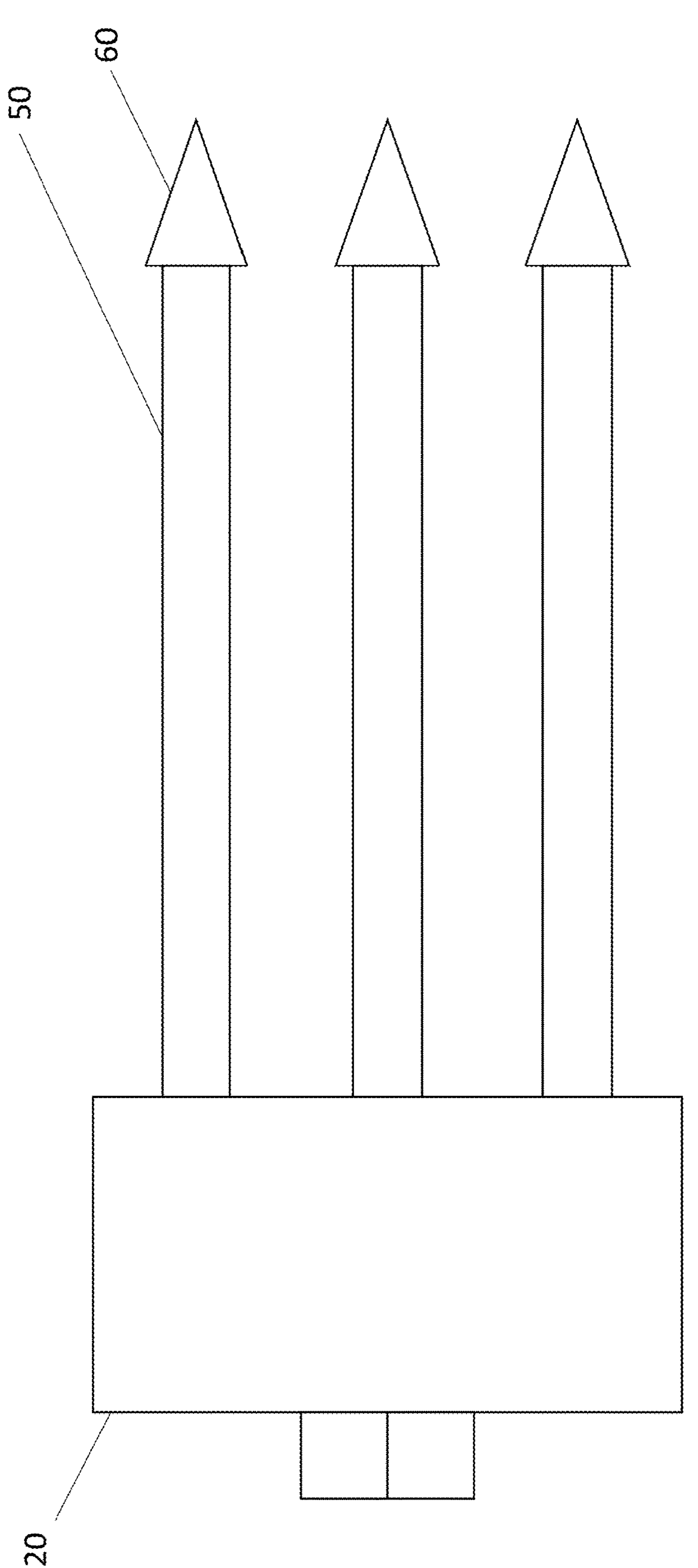
FIG. 6 is a side view of an embodiment of the instant invention, wherein rods connect to a reverse side of a head.
Figures 7A, 7B, 7C, 7D:
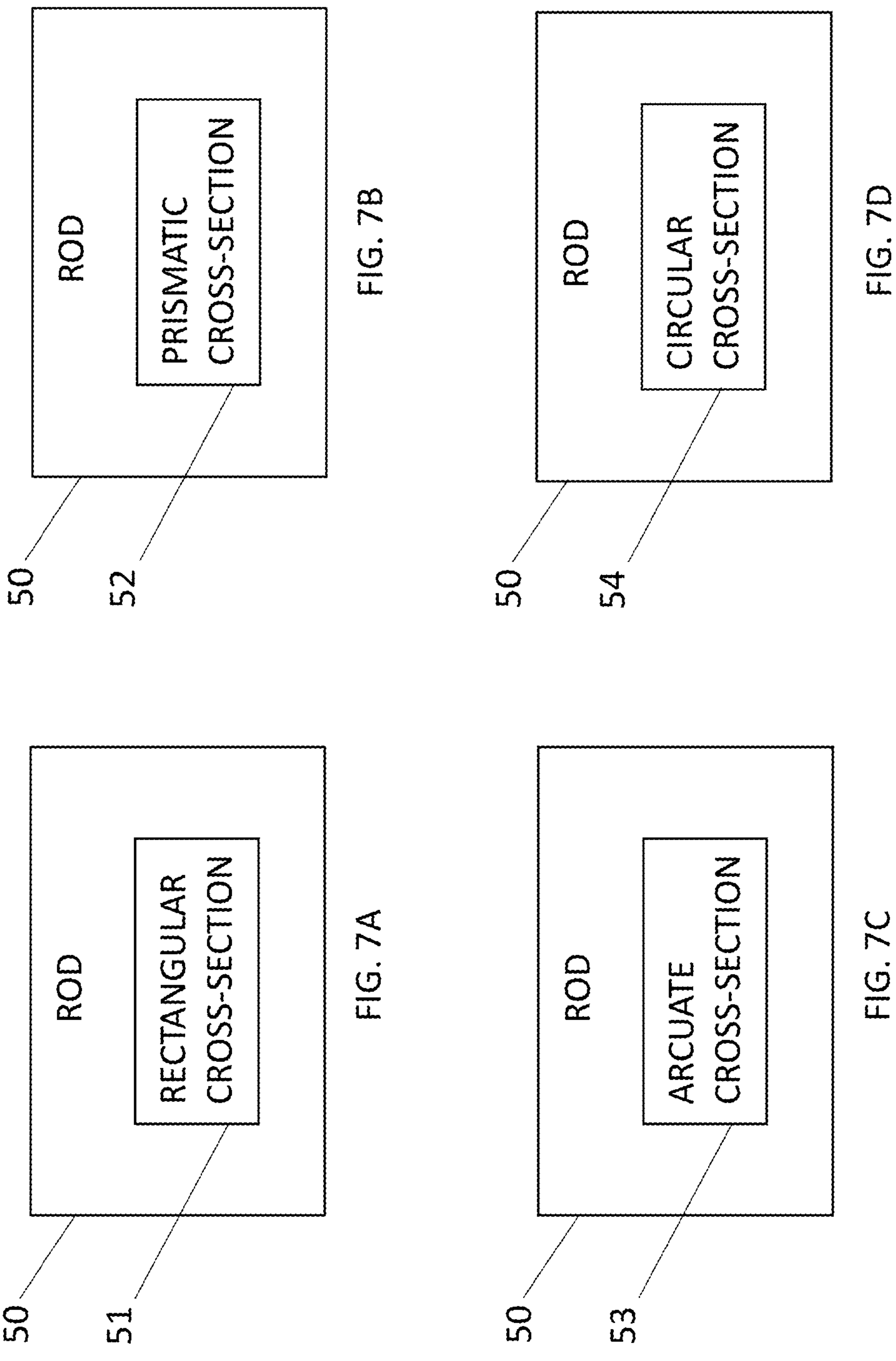
FIG. 7A is a block diagram of an illustrative pin having a rectangular cross-section in an embodiment of the instant invention.
FIG. 7B is a block diagram of an illustrative pin having a prismatic cross-section in an embodiment of the instant invention.
FIG. 7C is a block diagram of an illustrative pin having an arcuate cross-section in an embodiment of the instant invention.
FIG. 7D is a block diagram of an illustrative pin having a circular cross-section in an embodiment of the instant invention.

For example, as shown by way of illustration in FIGS. 4-6, in an embodiment of the invention with ½" diameter rods, the rods are retained inside of the head by about 1¼". Both ends of the pins have a threaded hole 70, in this embodiment of the invention. The hole 70 that seats the pin 42 is drilled about 1¼" long and has a ½" diameter, the rest of the hole being ¼" in diameter, in this embodiment of the invention. A standard bolt 80 holds the end of each pin 42 to the head 20, in this embodiment of the invention. There are six inches of each exposed rod 50 to where the respective cone is attached, in this embodiment of the invention.

In another embodiment of the invention, the head and the rods are unitary. In another embodiment of the invention, the rods are fused to the reverse side of the head.

An embodiment of the invention includes a singular pin configuration. In such an embodiment of the invention, the plurality of pins is placed into a soil matrix, and a vertical shaft supports a torque-applying component, as described herein. Using this embodiment of the invention, in initial rotation of the torque-applying component, the initial shear is often measured with the first torque through 90° and remolding measurements taken incrementally at subsequent larger angles, typically, after several full revolutions.

Another embodiment of the invention includes a compound pin and cone configuration. The compound pin and cone configuration includes a standard cone penetrometer as a central cone shaft with the plurality of pins, as described above, surrounding that shaft, making the central shaft perform dual duty. The operator applies initial downward force to make the cone index measurement followed by seating the surrounding plurality of pins and applying the rotational force to record the initial torque needed for initial shear failure followed by subsequent rotational force for continued remolding measurements.

The geotechnical apparatus 10 includes a standard torsional load cell 90 detachably connected to the obverse side of the head 20, as shown by way of illustration in FIG. 2. The torsional load cell 90 in operation measures a plurality of torques at a respective plurality of rotational angles. For the purpose of this patent application, the terms of torque and torsional load are interchangeable. An embodiment of the instant invention is mounted in or on a standard truck so as to be capable of penetration to a greater depths than would be otherwise possible by hand. Such an embodiment of the invention imparts a greater torque values via a motorized or electric system, with the truck as a reaction mass in both vertical insertion and torque application.

Optionally, the geotechnical apparatus 10 further includes a processor 100 communicating directly or indirectly with the vertical load cell 30 and the torsional load cell 90, as shown by way of illustration in FIGS. 1 and 2. For the purpose of this patent application, soil failure is a term of art and is defined as the soil's inability to sustain a current load, resulting in continuous deformation or displacement. For the purpose of this patent application, "vertical penetration strength value" is a term of art and is defined as vertical penetration stress at a particular displacement that induces soil failure. For the purpose of this patent application, "rotational shear strength value" is a term of art and is defined as rotational shear stress at a particular angular displacement that induces soil failure. The processor 100 converts the measured plurality of vertical loads into a plurality of vertical penetration shear strength values at the respective plurality of ground depths. The processor 100 converts the measured plurality of torques into a plurality of rotational shear strength values at the respective plurality of rotational angles. For example, the processor 100 uses the plurality of rotational shear strength values to determine a residual, or remolded, rotational shear strength of the soil/vegetation complex under investigation. For the purpose of this patent application, residual rotational shear strength and remolded rotational shear strength are interchangeable and are measured after a large deformation has been attained (e.g., after 2-3 full revolutions past maximum resistance). For example, the processor 100 uses the plurality of vertical penetration shear strength values and/or rotational shear strength values to determine peak shear strength of the soil/vegetation complex under investigation. For the purpose of this patent application, peak shear strength is a term of art and is defined as the maximum value of the shear stress, the material can sustain. For the purpose of this patent application, residual shear strength is a term of art and is defined as the minimum shear strength, which a soil experiences after large shear displacements under a given load have occurred. At peak shear strength, the soil carries the maximum possible stress. At a residual state, the soil has undergone a very large strain, and is thus the maximum possible stress it can develop, after such strains. Although both are soil failures, they are different types of soils failures. For example, according to one common strength model—Mohr-Coulomb—the cohesion and friction angle can be defined using the peak or residual values, and they can be very different. In alternative embodiment of the invention, other standard strength models are used.

An illustrative discussion of use of vertical loads and torques, as used in an embodiment of the invention, is found at Qiao, Huanhuan, The Practice and Development of T-Bar Penetrometer Tests in Offshore Engineering Investigation: A Comprehensive Review, Journal of Marine Science and Engineering, 1 Jun. 2023, pp. 1-31, Vol. 11, No. 6, MDPI, Basel, Switzerland, incorporated herein by reference. This article discusses use of penetrometers, including T-bar penetrometers. This article's solutions used for T-bar penetration are amenable for use in an embodiment of the invention in interpreting rotational shear as a rod moves through soil, generating plastic flow of sheared material around it, while force to move the rod is measured via a torsional load cell.

Optionally, the processor 100 generates a combined shear strength from at least the plurality of vertical penetration shear strength values at the respective plurality of ground depths and the plurality of rotational shear strength values at the respective plurality of rotational angles. For the purpose of this patent application, "combined shear strength" is a term of art and is defined as a soil's shear strength profile that includes a vertical penetration shear strength component and a rotational shear strength component. Optionally, the calculated combined shear strength is based in part on residual shear strength. Examples of how to calculate residual shear strength are found, for example, in Kayabali, K., et al., Shear strength of remolded soils at consistency limits, Canadian Geotechnical Journal, 2010, pp. 259-266, Vol. 47, No. 3, Canadian Publishing Science, Ottawa, Ontario, Canada, incorporated herein by reference; O'Kelly, Brendan C., Atterberg limits and remolded shear strength—Water content relationships." Geotechnical Testing Journal, 2013, pp. 939-947, Vol. 36, No. 6, ASTM, West Conshohocken, PA, USA, incorporated herein by reference; and Wu, Po-Kai, et al., Effects of specimen size and some other factors on the strength and deformation of granular soil in direct shear tests, Geotechnical Testing Journal, 2008, pp. 45-64, Vol. 31, No. 1, Canadian Publishing Science, Ottawa, Ontario, Canada, incorporated herein by reference.

In an embodiment of the invention, illustrative processing by the processor 100 is described as follows.

Geometry

In a geometry of an illustrative embodiment, the length of rod $L_r$ is the length of the portion of the rod that penetrates into the soil below ground level. Depending on the soil, the portion of the rod that penetrates into the soil below ground level may be the full length of the rod, or less than the full length, if initial penetration is terminated before that for any reason (e.g., due to stiffness of the soil). The length of the cone $L_c$ is the length of the cone used and is a function of a selected cone apex angle, α, e.g., 30°, and the cone base diameter $D_c$. Rod diameter is $D_r$.

The projected area of the cone is:

$$A_c = \frac{1}{2} D_c L_c$$

The length of the cone is a function of the desired cone diameter, and the selected cone angle, as follows:

$$L_c = \frac{D_c}{2\tan(\alpha)}$$

The projected area of the cone is thus:

$$A_c = \frac{D_c^2}{4\tan(\alpha)}$$

The projected area of the cone, replaced with an equivalent area of the rod is, for example, computed as follows:

$$A_{re} = D_r L_{re} = \frac{D_c^2}{4\tan(\alpha)}$$

Thus, the additional length of rod, with the same projected area as the cone, is, for example, computed as:

$$L_{re} = \frac{D_c^2}{4D_r\tan(\alpha)}$$

This length depends on the selections of the rod and cone base diameters, and the cone angle.

Shear Strength Calculation from the Vertical Insertion

Shear strength calculation from the vertical insertion is denoted as $S_v=f(z)$, i.e., a function of depth into the sediment, and as recorded during the initial (vertical insertion) phase of the device operation, wherein z is the depth of the vertical insertion of the pin into the soil.

Furthermore, the vertically-defined shear strength integral-averaged value, i.e., the total integral value of the entire shear strength profile with depth, up to the maximum penetration achieved (or the full, below-head, rod length, if fully buried) is, for example, given as follows:

$$S_{v\,ave} = \frac{1}{z_{max}}\int_0^{z_{max}} S_v(z)dz$$

Shear Strength from Rotational Testing Phase

A force diagram for an embodiment of the invention can be thought of as follows. The center of a head is considered to be the center of rotation. A pin is located at R, a radius of rotation and is the distance from the center of rotation (i.e., the center of the head), the rods being equidistant form the center. T is the total torque applied to the head, and F is the force that each rod is applying to the soil/vegetation complex under investigation.

The balance of moments is, for example:

$$T = 3FR.$$

In this example, the number "3" indicates an embodiment of the invention having 3 rods. In alternative embodiments of the invention having different numbers of rods, the correct number of rods would be substituted for the number "3".

The force F is generally a function of shear strength determined in rotation, or $S_r$. The shear strength determined in rotation is distinguished from the shear strength as determined incrementally, during the initial penetrometer burial stage of the device operation and is here defined as $S_v$—with indexes "v"—for vertical phase of testing, and "r"—for rotational phase of testing. These values of shear strength are nominally identical in uniform soil that does not have any heterogenous inclusions (e.g., vegetation, above-ground, below-ground, or both) or any synthetic geotechnical materials.

In Clean Soils (i.e., No Heterogeneous/Discontinuous Matter)

For clean soils, where the contribution of vegetative materials (e.g., below-ground biomass, or a combination of below-ground biomass and above-ground biomass) or geotextile materials is non-existent or negligible, the following solution for the $S_r$— shear strength from rotational component is, for example, derived:

$$F = \frac{T}{3R}$$

$$\sigma_r = \frac{F}{A_{re}},$$

where $\sigma_r$ is the shear stress imposed in soil as a result of the rod translational motion along an arc and $A_{re}$—was defined above. This stress at failure (i.e., any time there is motion)—a solution by Randolph, M. F., "Characterization of soft sediments for offshore applications," Proceedings of the Second International Conference on Site Characterization, ISC-2, 19-22 Sep. 2004, pp. 209-231, International Society for Soil Mechanics and Geotechnical Engineering, Porto, Portugal, incorporated herein by reference, is, for example, utilized as developed for motion of a bar through soil. Other potential solutions may be utilized. The following relation is then generally adapted, linking the stress imposed by the moving rod to the internal shear stress (i.e. strength) in the mass of soil that is resisting this motion:

$$S_r = \frac{T}{3RD_rL_{re}N_r},$$

where $N_r$, is a non-dimensional factor, responsible for including the contribution of the bulk of the sheared soil, $\sigma_r=S_rN_r$.

$S_r$ is also a function of the rotation angle, henceforth defined as θ, so $S_r=f(\theta)$.

Combined Shear Strength Value

In clean soils, a combined average sear strength value is, for example, calculated for the full burial depth of the cones in a number of ways, with, e.g., the simplest one computing an average:

$$S_c = \frac{1}{2}\left[\frac{1}{z_{max}}\int_0^{z_{max}} S_v(z)dz + S_r\right],$$

where $S_c$ is the combined average shear strength of soil—and is derived from both, the vertically-measured profile of $S_v$ and the rotational aggregate value of $S_r$.

In clean soils, e.g., CHANEY, R. C. et al., "Measurement of residual/remolded vane shear strength of marine sediments," Vane Shear Strength Testing in Soils: Field and Laboratory Studies, 1988, pp. 166-181, American Society for Testing and Materials, West Conshohocken, PA, USA, incorporated herein by reference, the soil resistance in rotational failure occurs, for example, between 2° and 15° of rotation. In vegetative soils, a failure, for example, occurs at substantially greater rotational values, and often past the 90° of rotation. In such cases, i.e., those wherein the heterogeneity of the soils is not considered sufficiently complex, the averaged Sc value is, for example, used to represent the shear strength of the soil complex.

If the peak rotational shear resistance occurs at greater than 200 of rotation, the soil is, for example, considered complex and heterogeneous, including possible significant contribution from organic and/or inorganic discontinuous components (e.g., roots, grids, membranes). In these cases, the averaging of the vertical and rotational shear strength components is, for example, not appropriate, and the overall measure peak $S_r$, as recorded at larger rotation angles, is used to represent the shear strength of the soil complex.

Complex Materials

In complex materials with below-ground biomass or both below-ground biomass and above-ground biomass (or geotextiles), the shear strength in vertical phase of testing $S_v$ profile is utilized with depth and then contributions of each other component are incrementally retrieved, if present. The other components include, for example, the rotational shear strength of oil and below-ground biomass $S_{r\_BGB}$, the rotational shear strength of soil including below and above-ground biomass $S_{R\_BAGB}$, and/or the residual (or remolded) values of both (as discussed below). In other words, the equation for the applied torque T is as follows:

$$T = 3R(F_{soil} + F_{BGB} + F_{AGB}),$$

where the force contributing to the resistance is composed of a component due to soil resistance (as above, in clean soils), one due to above-ground biomass and one due to below-ground biomass, separately.

The shear strength profile from the vertical phase of testing, $S_v(z)$ is then used, for example, to compute the soil-only component of the rotational resistance. Furthermore, if the above-ground biomass is first removed, then the test only includes a contribution of soil and the below-ground biomass. Because soil contribution is, for example, computed as indicated above, the rotational strength contribution due to below-ground biomass only is, for example, calculated as:

$$F_{BGB} = \frac{T}{3R} - F_s$$

and $$S_{BGB} = \frac{F_{BGB}}{D_r L_{re}}$$

In the next step, a location nearby may be tested again, and this time, without removing the above-ground biomass. Now having computed the below-ground biomass contribution and the soil contributions separately:

$$F_{AGB} = \frac{T}{3R} - F_s - F_{BGB}.$$

Additional Indexes

The following additional indexes are, for example, used in characterizing simple and complex soils:

A Soil Strength Index is, for example, a Matrix soil strength index:

$$SSI = SSI_M = \frac{s_r(\text{if peak at } \theta < 20\ deg)}{S_{v\,ave}}$$

Complex matrix soil strength index:

$$SSI = I_C = \frac{s_r(\text{if peak at } \theta > 20\ deg)}{S_{v\,ave}}$$

As indicated by the above equations, the Soil Strength Index ("SSI"), for example, thus represents a simple material or a complex material as a ratio of the rotational shear strength value to the vertically-defined shear strength integral-averaged value.

In practice, the procedure for the vertical shear strength test is, for example, preferably restarted, if a discontinuous matter (e.g., a single root) is encountered, thus skewing interpretation of the soil matrix characterization to that of a single heterogeneity, which may not be representative of other heterogeneities present, or the overall soil matrix involved.

One of the ordinary skill in the art will readily appreciate that the rotation component of an embodiment of the invention yields a better representation than conventional geotechnical instruments, e.g. a vane shear device, because of the former's ability to engage multiple such discontinuities present in a tested soil volume.

Remolding Conditions and Remolded Shear Strength

An embodiment of the invention is able to measure remolded shear strength of complex soil, $S_{rr}$, as noted above. For that purpose, an illustrative operating procedure includes an amount of rotational deformation needed to attain a constant post-peak shear response that is not changing with additional rotational deformation. This post-peak regime is, for example, attained at a range of rotational angles, depending on the complex structure (i.e., with or without vegetation, geotextiles etc.). According to standard geotechnical procedures, in pure (i.e., non-complex) soils, this is typically defined as shear strength after five to ten full revolutions.

Additional shearing resistance provided by the heterogeneous or discontinuous component of the complex soil (i.e., having above-ground biomass, below-ground biomass, and/or geotextiles) is expected to be reduced to its residual, or remolded, state as well at the rotational deformation of five to ten revolutions. In this case, the standard procedure appears adequate and needs no further adjustment.

Furthermore, complex soil sensitivity, $ST_r$, is, for example, also measured, using the same procedure as in, ASTM Standard D2573, "Standard Test Method for Field Vane Shear Test in Cohesive Soil," 2008, doi: DOI: 10.1520/C0033-03A, ASTM International, West Conshohocken, PA, incorporated herein by reference, as a ratio of peak rotational shear strength to the residual/remolded value: For example, complex soil sensitivity, $ST_r$, is:

$$ST_r = S_r/S_{rr}.$$

Optionally, the head 20 includes a center. Each pin 42 of the plurality of pins 40 is located at a same distance from the center.

Optionally, the plurality of pins 40 includes three pins set 120° apart. In an embodiment of the invention, three pins at 120° apart achieve balance and allow an operator to capture first shear failure and read the torque (typically thought to occur within first 90°) without interference from the soil remolding effects by a rotationally preceding pin.

Figure 8B:
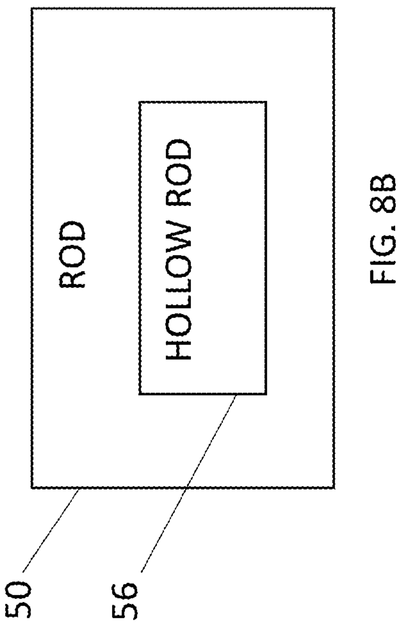
FIG. 8B is a block diagram of an illustrative rod including a hollow rod in an embodiment of the instant invention.
Figure 8A:
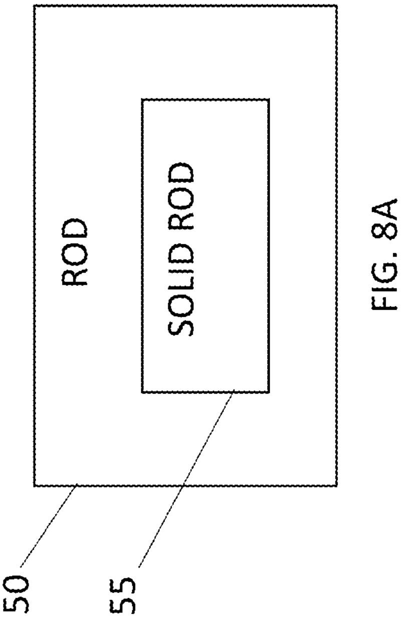
FIG. 8A is a block diagram of an illustrative rod including a solid rod in an embodiment of the instant invention.

Optionally, the rod 50 includes a rectangular cross-section 51, a prismatic cross-section 52, an arcuate cross-section 53, or a circular cross-section 54, as shown by way of illustration in FIGS. 7A-7D, respectively. Optionally, the rod includes a solid rod 55 or a hollow rod 56, as shown by way of illustration in FIGS. 8A and 8B, respectively.

Figure 9B:
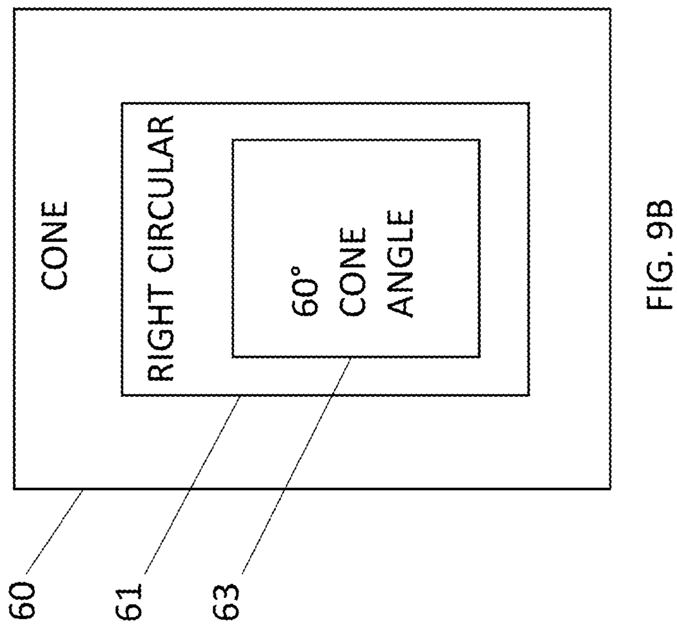
FIG. 9B is a block diagram of an illustrative right circular cone having a 60° cone angle in an embodiment of the instant invention.
Figure 9A:
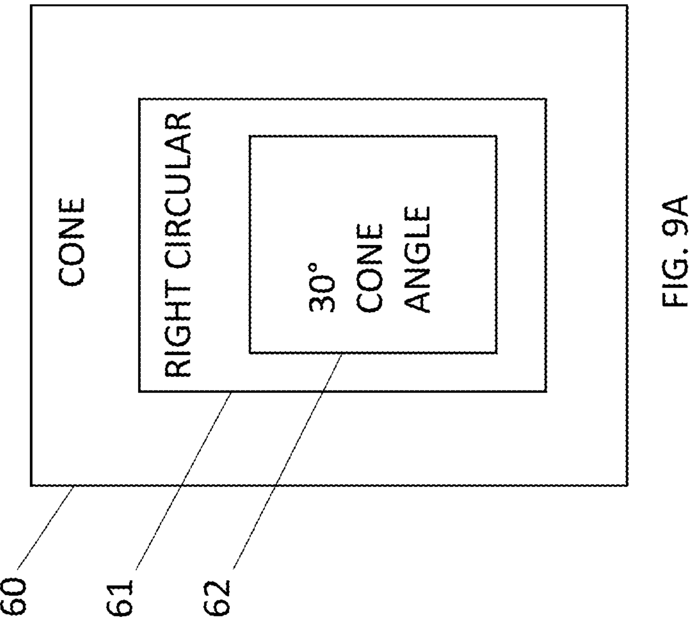
FIG. 9A is a block diagram of an illustrative right circular cone having a 30° cone angle in an embodiment of the instant invention.

Optionally, the cone includes a right circular cone. Optionally, the cone includes a cone angle, the cone angle being 30° or 60°, as shown by way of illustration in FIGS. 9A and 9B, respectively.

Figure 10:
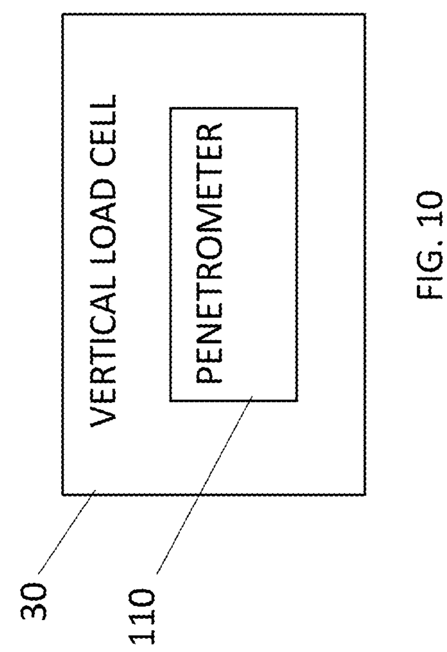
FIG. 10 is a block diagram of an illustrative vertical load cell including a penetrometer in an embodiment of the instant invention.

Optionally, the vertical load cell 30 includes a standard penetrometer 110, as shown in FIG. 10.

Figure 11:
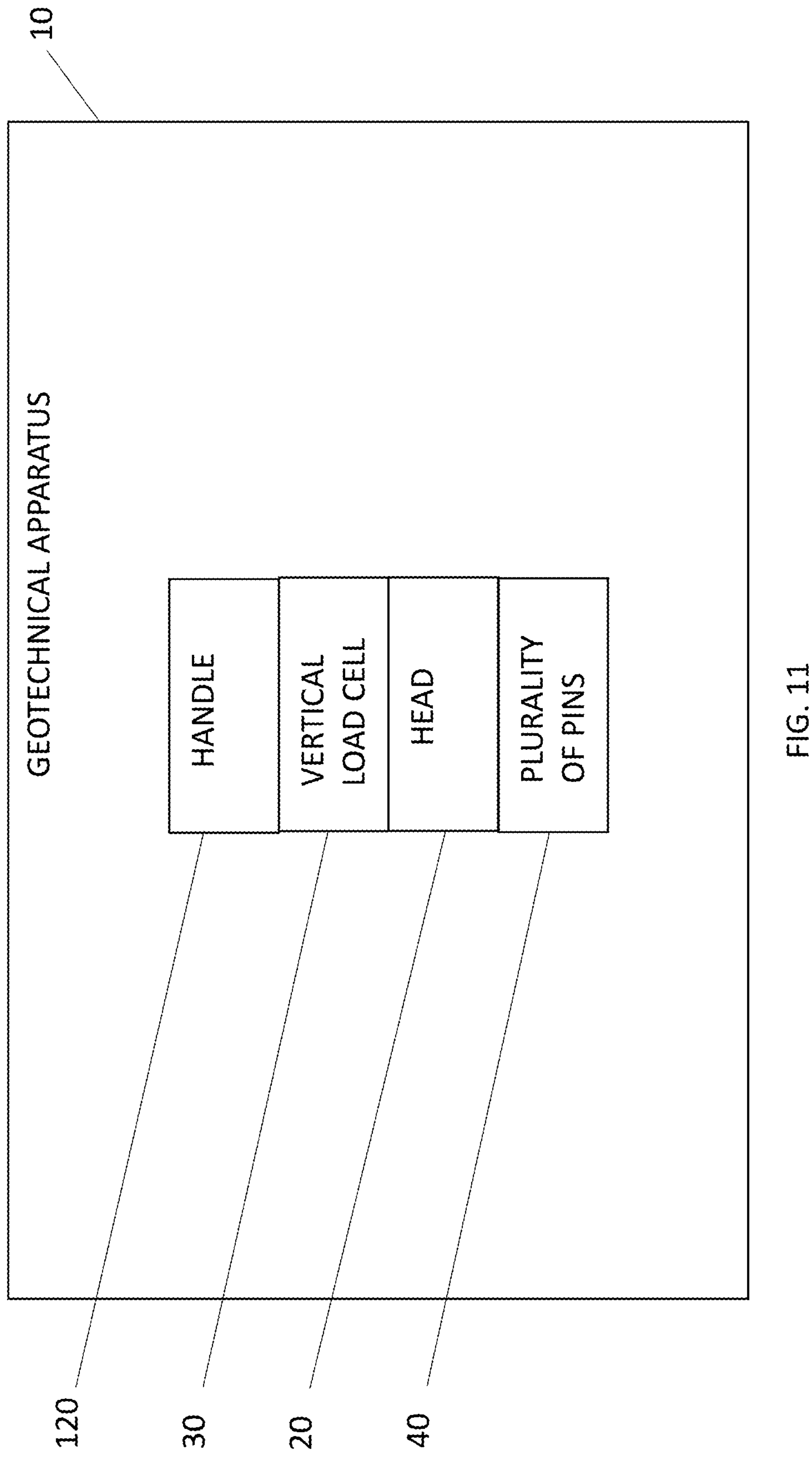
FIG. 11 is a block diagram of an illustrative handle connected to a vertical load cell in an embodiment of the instant invention.

Optionally, the geotechnical apparatus 10 further includes a standard handle 120 connected to the head 20 for manually driving the head to the plurality of ground depths, as shown by way of illustration in FIG. 11.

Figure 12:
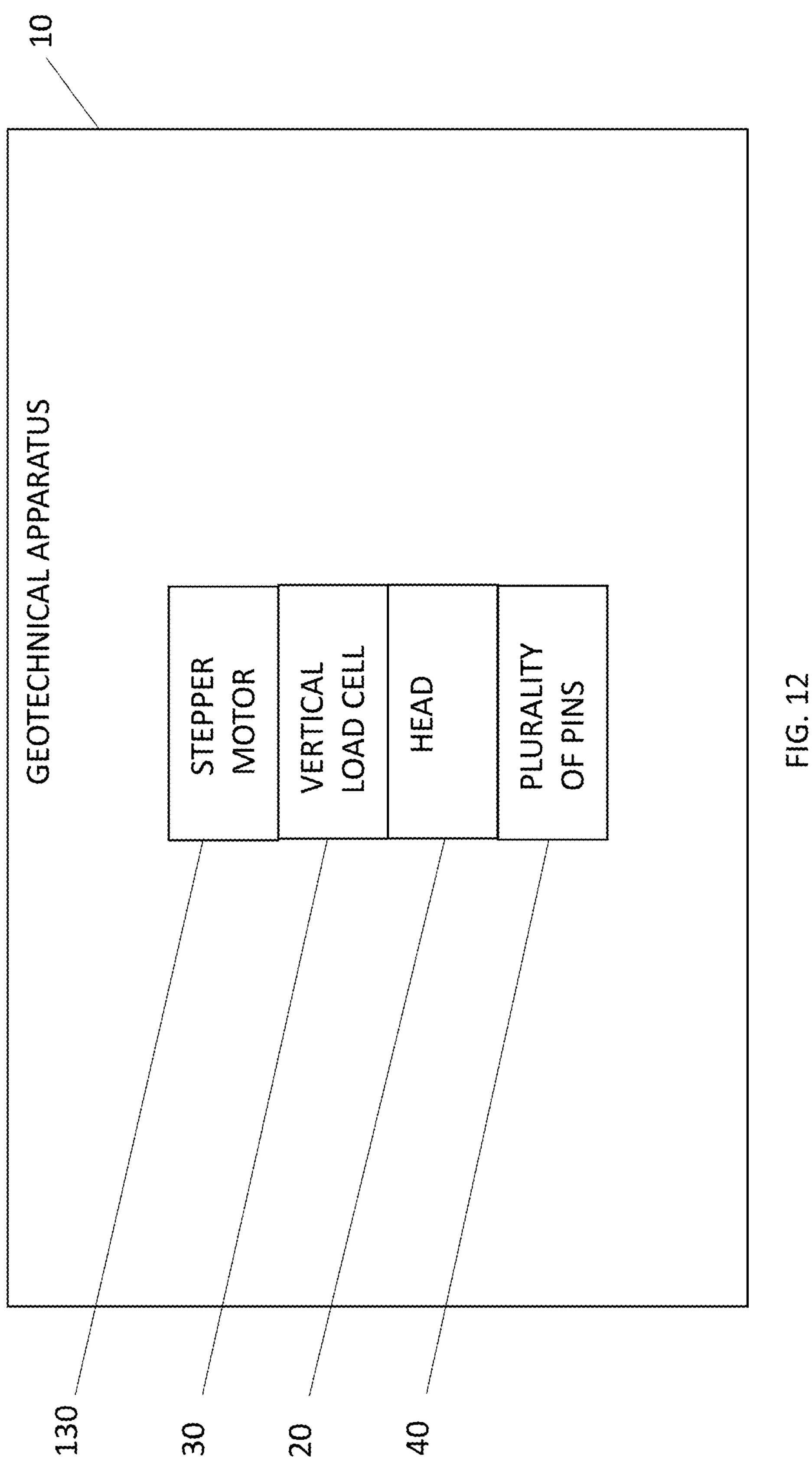
FIG. 12 is a block diagram of an illustrative stepper motor connected to a vertical load cell in an embodiment of the instant invention.

Optionally, the geotechnical apparatus 10 further includes a standard stepper motor 130 connected to the head 20, as shown by way of illustration in FIG. 12. In operation, the stepper motor 130 drives the head to the plurality of ground depths.

Figure 13:
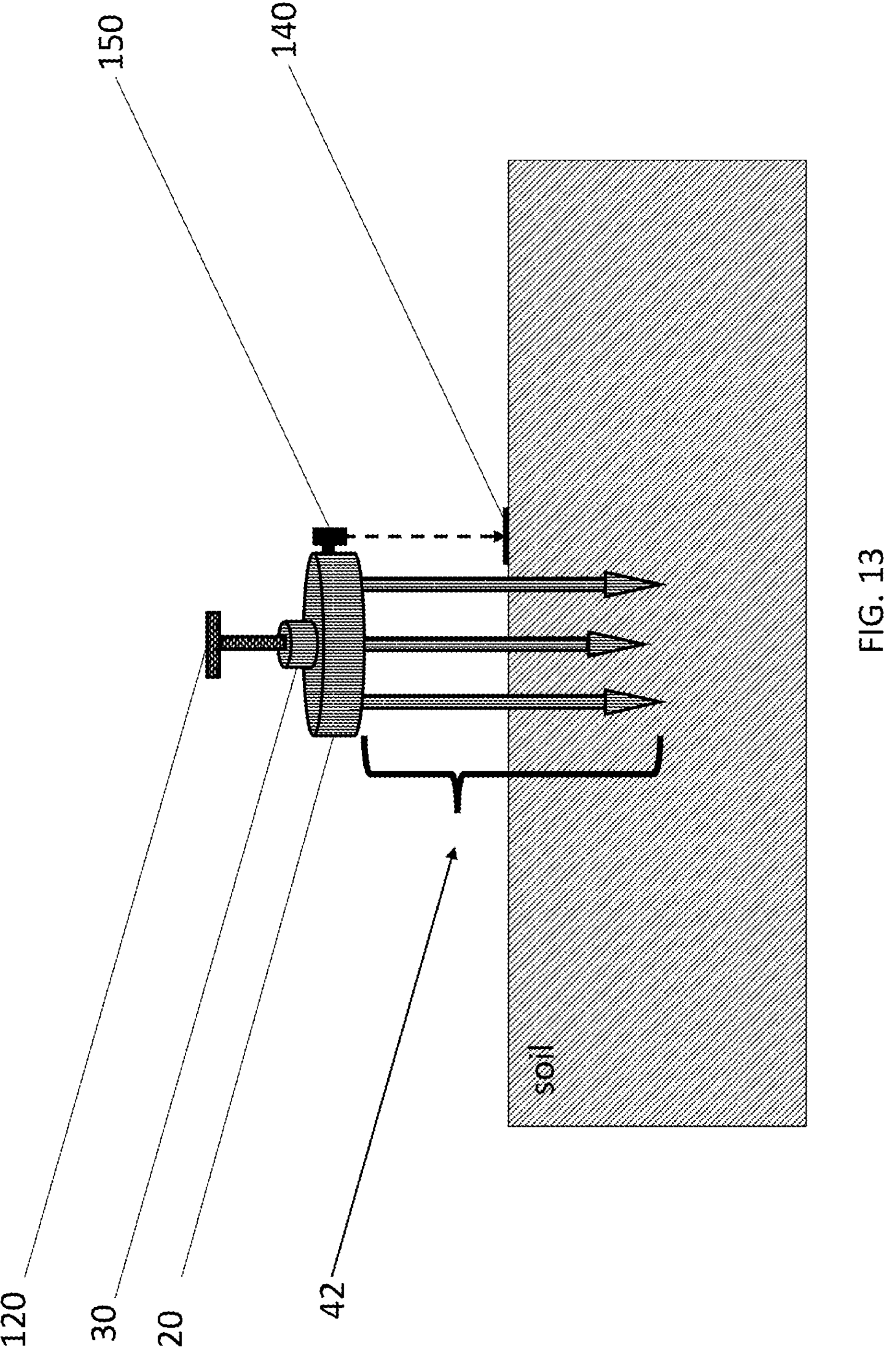
FIG. 13 is a perspective view of an embodiment of the instant invention, for example, in a vertical shearing testing mode
Figures 14A, 14B:
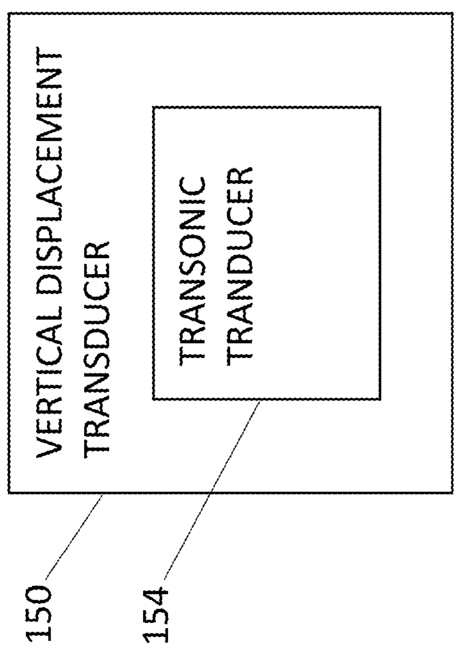
FIG. 14A is a block diagram of an illustrative vertical displacement transducer including a linear variable differential transducer in an embodiment of the instant invention.
FIG. 14B is a block diagram of an illustrative vertical displacement transducer including a transonic transducer in an embodiment of the instant invention.
Figure 16:
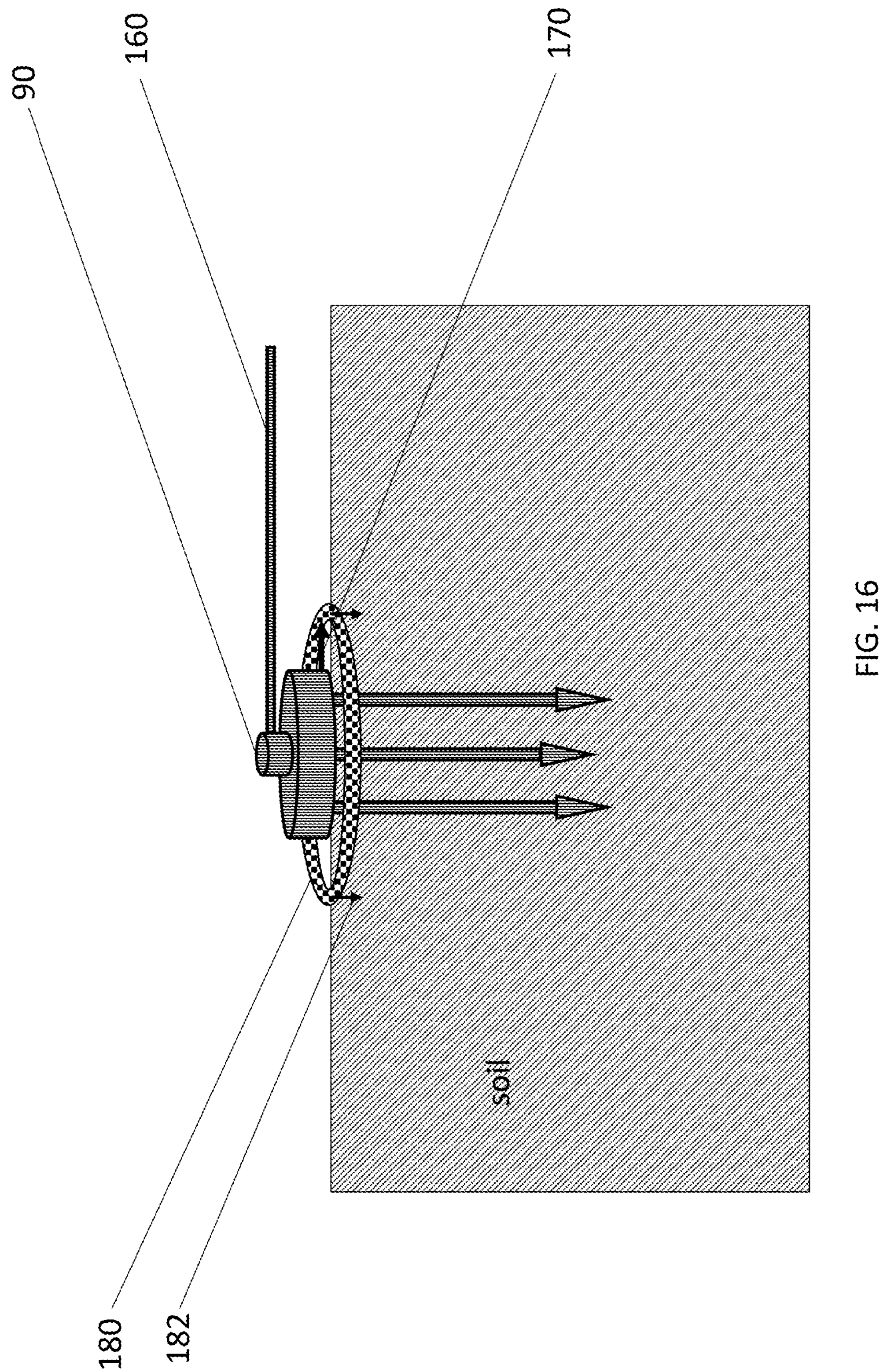
FIG. 16 is a perspective view of an embodiment of the instant invention, for example, in a manual rotational vertical shearing testing mode.
Figure 17:
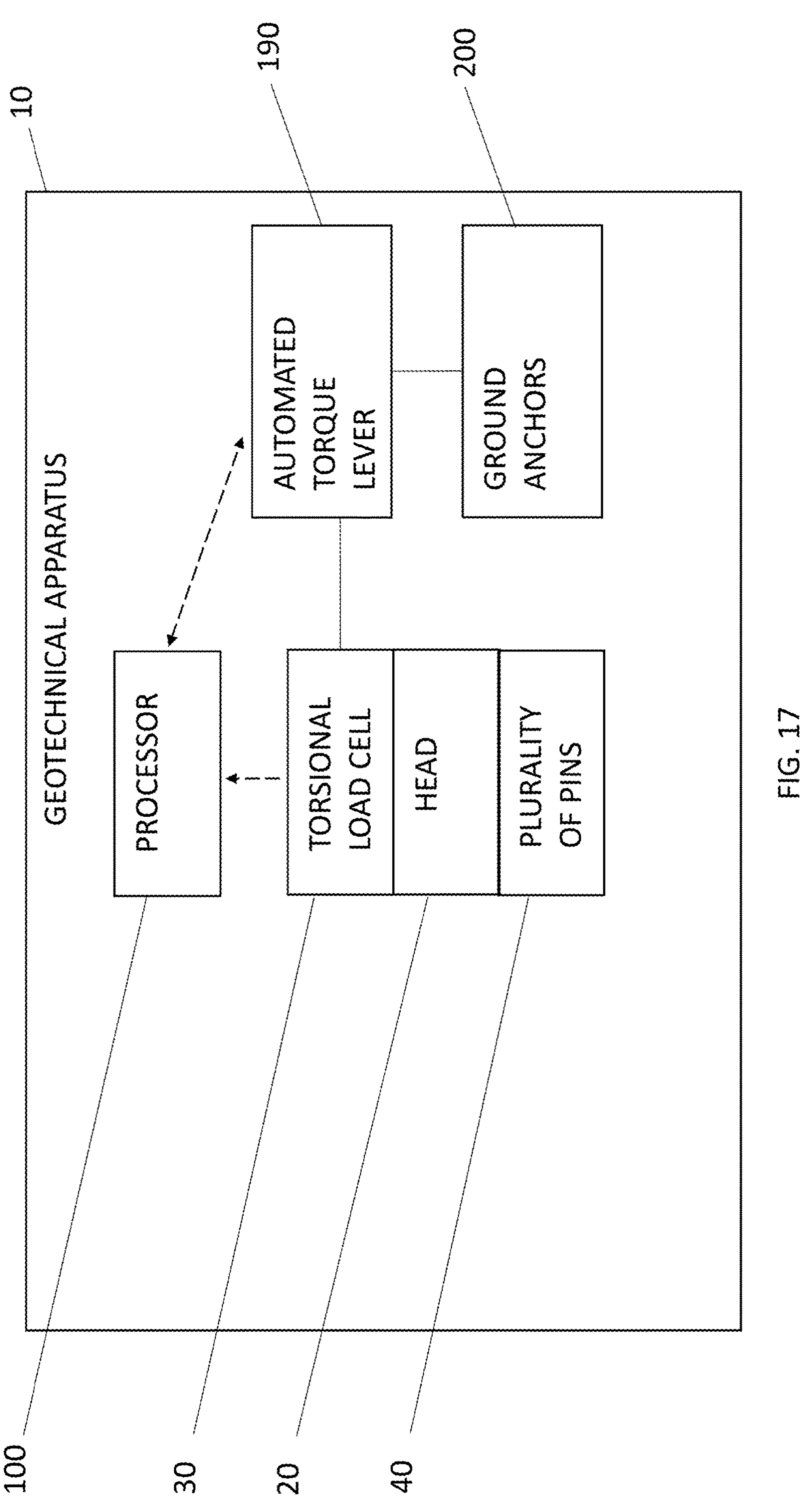
FIG. 17 is a block diagram of an embodiment of the instant invention including a torque driver having ground anchors.
Figure 18:
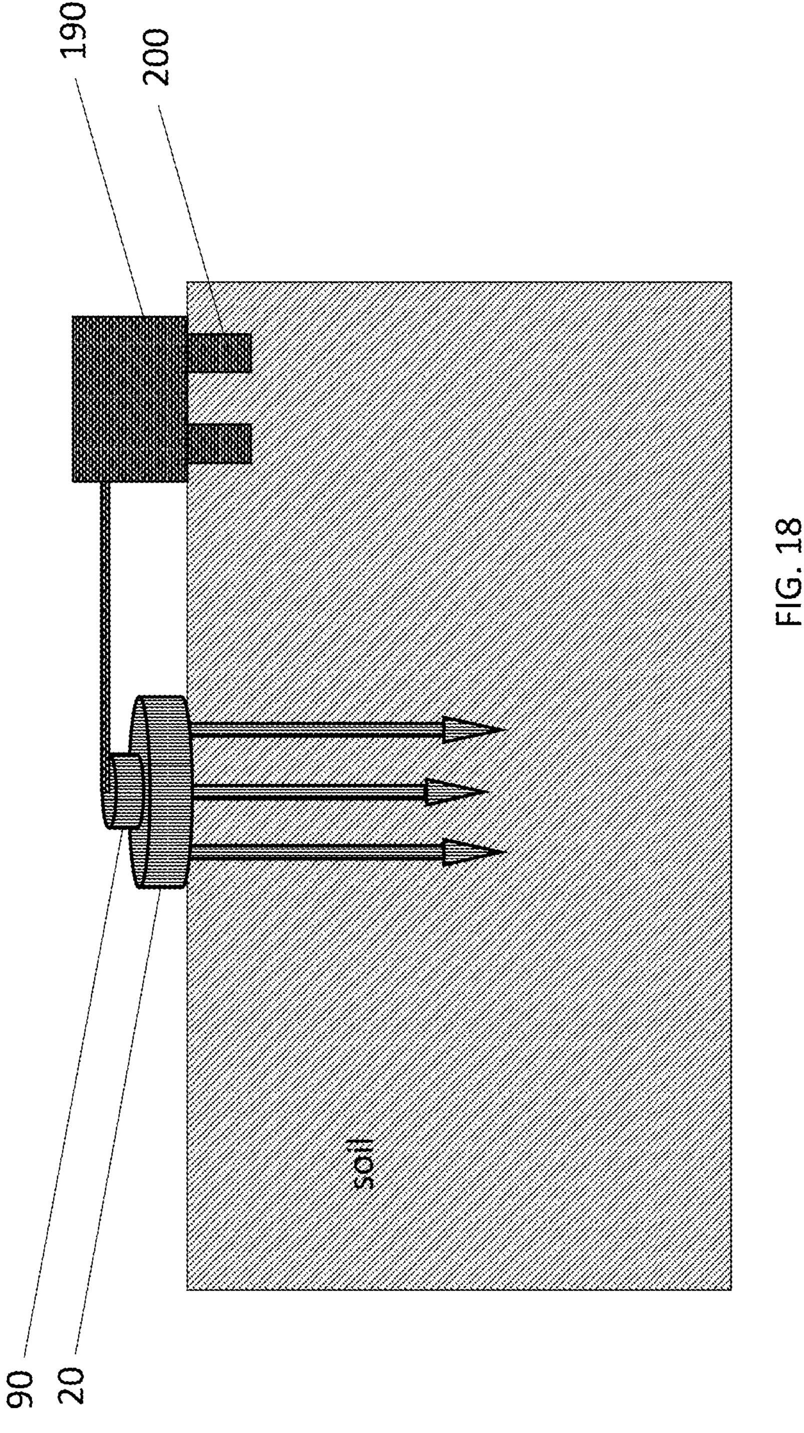
FIG. 18 is a perspective view of an embodiment of the instant invention, for example, in an automated rotational vertical shearing testing mode.

Optionally, the geotechnical apparatus 10 further includes a standard soil surface plate 140, as shown by way of illustration in FIGS. 1 and 13. In FIGS. 13, 16, and 18, the label "soil" includes pure soil (i.e., a mixture of inorganic and organic continuous matter), soil with vegetation complex, and/or soil with embedded synthetic geotechnical materials. The geotechnical apparatus 10 also includes a standard detachable vertical displacement transducer 150 connected to the head 20 and communicating with the soil surface plate 140. The vertical displacement transducer 150 generates a plurality of vertical displacement values corresponding to the respective plurality of ground depths and communicating the plurality of vertical displacement values to the processor 100. In an embodiment of the invention, an operator manually enters the respective plurality of vertical displacement values, or the respective plurality of ground depths, to the processor 100. In another embodiment of the invention, the vertical displacement transducer transmits the respective plurality of vertical displacement values to the processor. Optionally, the vertical displacement transducer 150 includes a linear variable differential transducer 152 or a transonic transducer 154, as shown by way of illustration in FIG. 14, respectively.

Figure 15:
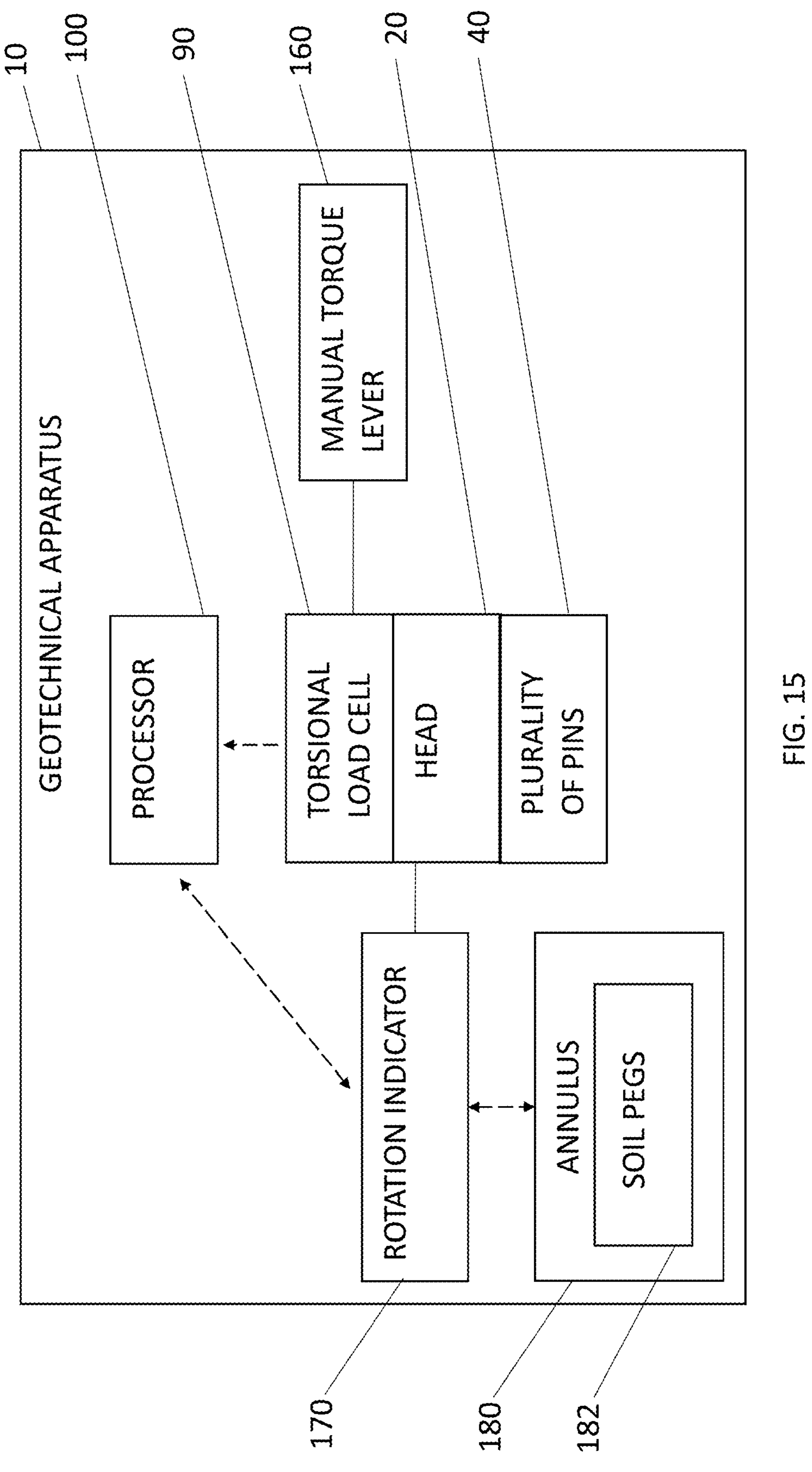
FIG. 15 is a block diagram of an embodiment of the instant invention including a manual torque lever, a rotation indicator, and an annulus having soil pegs.

Optionally, the geotechnical apparatus 10 further includes a standard manual torque lever 160 connected to the torsional load cell 90, as shown by way of illustration in FIGS. 15 and 16. In operation, the manual torque lever 160 applies torque to the torsional load cell 90. The geotechnical apparatus 10 also includes a standard detachable rotation indicator 170 connected to the head 20. The rotation indicator 170 indicates the respective plurality of rotational angles. In an embodiment of the invention, an operator manually enters the respective plurality of rotational angles to the processor 100. In another embodiment of the invention, the rotation indicator 170 transmits the respective plurality of rotational angles to the processor 100.

Optionally, the geotechnical apparatus 10 further includes a standard detachable annulus 180, as shown in FIGS. 15 and 16. The annulus 180 includes a plurality of standard soil pegs 182 and is graduated in degrees. The rotation indicator 170 cooperates with the annulus 180.

Optionally, the geotechnical apparatus 10 further includes a standard torque driver 190 connected to the torsional load cell 90, as shown by way of illustration in FIGS. 17, 18, and 19A-19C. In operation, the torque driver 190 applies torque to the torsional load cell 90. The torque driver 190 includes a standard rotational variable displacement transducer 192, a standard motor-driven torque lever 194, or a standard electrically driven torque lever 196, a standard automated geared rod 198, such as shown by way of illustration in FIGS. 19A-19D, respectively. The torque driver 190 includes an end, and a plurality of standard ground anchors 200 are connected to the end of the torque driver.

Optionally, one or more portions of the invention operate in a standard computing operating environment, for example, a desktop computer, a laptop computer, a mobile computer, a server computer, and the like. Although the invention is described in the general context of program modules that run on an operating system on a personal computer, those skilled in the art will recognize that the invention may also be implemented in combination with other types of computer systems and program modules.

Generally, program modules include routines, programs, components, data structures, and other types of structures that perform particular tasks or implement particular abstract data types. Moreover, those skilled in the art will appreciate that the invention may be practiced with other computer system configurations, including hand-held devices, multiprocessor systems, microprocessor-based or programmable consumer electronics, minicomputers, mainframe computers, autonomous embedded computers, and the like. The invention may also be practiced in distributed computing environments where tasks are performed by remote processing devices that are linked through a communications network. In a distributed computing environment, program modules may be located in both local and remote memory storage devices.

An illustrative operating environment for embodiments of the invention is described as follows. A computer comprises a general purpose desktop, laptop, handheld, mobile or other type of computer (computing device) capable of executing one or more application programs. The computer includes at least one central processing unit ("CPU"), a system memory, including a random access memory ("RAM") and a read-only memory ("ROM"), and a system bus that couples the memory to the CPU. A basic input/output system containing the basic routines that help to transfer information between elements within the computer, such as during startup, is stored in the ROM. The computer further includes a mass storage device for storing an operating system, application programs, and other program modules.

The mass storage device is connected to the CPU through a mass storage controller connected to the bus. The mass storage device and its associated computer-readable media provide non-volatile storage for the computer. Although the description of computer-readable media contained herein refers to a mass storage device, such as a hard disk or CD-ROM drive, it should be appreciated by those skilled in the art that computer-readable media can be any available media that can be accessed or utilized by the computer.

By way of example, and not limitation, computer-readable media comprise computer storage media and communication media. Computer storage media includes non-transitory, non-volatile, removable and non-removable media implemented in any method or technology for storage of information such as computer-readable instructions, data structures, program modules or other data. Such non-transitory computer storage media includes, but is not limited to, RAM, ROM, EPROM, EEPROM, flash memory or other solid state memory technology, CD-ROM, digital versatile disks ("DVD"), or other optical storage, magnetic cassettes, magnetic tape, magnetic disk storage or other magnetic storage devices, or any other tangible non-transitory medium which can be used to store the desired information and which can be accessed by the computer.

According to various embodiments of the invention, the computer may operate in a networked environment using logical connections to remote computers through a network, such as a local network, the Internet, etc. for example. The computer may connect to the network through a network interface unit connected to the bus. It should be appreciated that the network interface unit may also be utilized to connect to other types of networks and remote computing systems.

The computer optionally also include an input/output controller for receiving and processing input from a number of other devices, including a keyboard, mouse, sensor, load cell, transducer, etc. Similarly, an input/output controller may provide output to a display screen, a printer, or other type of output device.

As mentioned briefly above, a number of program modules and data files may be stored in the mass storage device and RAM of the computer, including an operating system suitable for controlling the operation of a networked personal computer. The mass storage device and RAM may also store one or more program modules. In particular, the mass storage device and the RAM may store application programs, such as a software application, for example, a word processing application, a spreadsheet application, a slide presentation application, a database application, etc.

It should be appreciated that various embodiments of the instant invention may be implemented as a sequence of computer-implemented acts or program modules running on a computing system and/or as interconnected machine logic circuits or circuit modules within the computing system. The implementation is a matter of choice dependent on the performance requirements of the computing system implementing the invention. Accordingly, logical operations including related algorithms can be referred to variously as operations, structural devices, acts or modules. It will be recognized by one skilled in the art that these operations, structural devices, acts and modules may be implemented in software, firmware, special purpose digital logic, and any combination thereof without deviating from the spirit and scope of the instant invention as described herein.

Although a particular feature of the disclosure may have been illustrated and/or described with respect to only one of several implementations, such feature may be combined with one or more other features of the other implementations as may be desired and advantageous for any given or particular application. Also, to the extent that the terms "including", "includes", "having", "has", "with", or variants thereof are used in the detailed description and/or in the claims, such terms are intended to be inclusive in a manner similar to the term "comprising".

As used herein, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

All documents mentioned herein are hereby incorporated by reference for the purpose of disclosing and describing the particular materials and methodologies for which the document was cited.

Although the instant invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

This written description sets forth the best mode of the invention and provides examples to describe the invention and to enable a person of ordinary skill in the art to make and use the invention. This written description does not limit the invention to the precise terms set forth. Thus, while the invention has been described in detail with reference to the examples set forth above, those of ordinary skill in the art may effect alterations, modifications and variations to the examples without departing from the scope of the invention.

These and other implementations are within the scope of the following claims.

What is claimed is:

1. An apparatus comprising:

a head comprising an obverse side and a reverse side;

a vertical load cell detachably connected to said obverse side;

a plurality of pins connected to said reverse side, each pin of said plurality of pins comprising a rod and a cone connected to said rod, said rod comprising a rod diameter, said cone comprising a cone diameter. said cone diameter being larger than said rod diameter, said plurality of pins in contact with soil and comprising a plurality of vertical loads at a respective plurality of ground depths, said vertical load cell in operation measuring the plurality of vertical loads at the respective plurality of ground depths; and a torsional load cell detachably connected to said obverse side, said plurality of pins in contact with soil and comprising a plurality of torques at a respective plurality of rotational angles, said torsional load cell in operation measuring a the plurality of torques at a the respective plurality of rotational angles.

2. The apparatus according to claim 1, wherein said head comprises a center, wherein said each pin of said plurality of pins is located at a same distance from said center.

3. The apparatus according to claim 1, wherein said plurality of pins comprise three pins set 120° apart.

4. The apparatus according to claim 1, wherein said rod comprises one of a rectangular cross-section, a prismatic cross-section, an arcuate cross-section, and a circular cross-section, wherein said rod comprises one of a solid rod and a hollow rod.

5. The apparatus according to claim 1, wherein said cone comprises a right circular cone, wherein said cone comprises a cone angle, the cone angle comprising one of 30° and 60°.

6. The apparatus according to claim 1, wherein said vertical load cell comprises a penetrometer.

7. The apparatus according to claim 1, further comprising:

a handle connected to said head for manually driving said head to the plurality of ground depths.

8. The apparatus according to claim 1, further comprising:

a stepper motor connected to said head and in operation driving said head to the plurality of ground depths.

9. The apparatus according to claim 1, further comprising:

a manual torque lever connected to said torsional load cell and in operation applying torque to said torsional load cell; and a detachable rotation indicator connected to said head, said rotation indicator indicating the respective plurality of rotational angles.

10. The apparatus according to claim 9, wherein said rotation indicator transmits the respective plurality of rotational angles to said processor.

11. The apparatus according to claim 9, further comprising:

a detachable annulus comprising a plurality of soil pegs and is graduated in degrees, the rotation indicator cooperating with said annulus.

12. The apparatus according to claim 1, further comprising:

a torque driver connected to said torsional load cell and in operation applying torque to said torsional load cell, said torque driver comprising one of a rotational variable displacement transducer, a motor-driven torque lever, an electrically driven torque lever, and an automated geared rod, said torque driver comprising an end;

a plurality of ground anchors connected to said end of said torque driver.

13. An apparatus comprising:

a head comprising an obverse side and a reverse side;

a vertical load cell detachably connected to said obverse side;

a plurality of pins connected to said reverse side, each pin of said plurality of pins comprising a rod and a cone connected to said rod, said plurality of pins in contact with soil comprising a plurality of vertical loads at a respective plurality of ground depths, said vertical load cell in operation measuring the plurality of vertical loads at the respective plurality of ground depths;

a torsional load cell detachably connected to said obverse side, said plurality of pins in contact with soil comprising a plurality of torques at a respective plurality of rotational angles, said torsional load cell in operation measuring the plurality of torques at the respective plurality of rotational angles; and a processor communicating one of directly and indirectly with said vertical load cell and said torsional load cell, said processor converting the measured plurality of vertical loads into a plurality of vertical penetration shear strength values at the respective plurality of ground depths, said processor converting the measured plurality of torques into a plurality of rotational shear strength values at the respective plurality of rotational angles.

14. The apparatus according to claim 13, wherein said processor generates a combined shear strength from at least the plurality of vertical penetration shear strength values at the respective plurality of ground depths and the plurality of rotational shear strength values at the respective plurality of rotational angles.

15. The apparatus according to claim 13, further comprising:

soil surface plate; and a detachable vertical displacement transducer connected to said head and communicating with said soil surface plate, said vertical displacement transducer generating a plurality of vertical displacement values corresponding to the respective plurality of ground depths and communicating the plurality of vertical displacement values to said processor.

16. The apparatus according to claim 15, wherein said vertical displacement transducer comprises one of a linear variable differential transducer and a transonic transducer.

* * * * *